United States Patent [19]
Kalis

[11] Patent Number: 5,609,624
[45] Date of Patent: Mar. 11, 1997

[54] REINFORCED VASCULAR GRAFT AND METHOD OF MAKING SAME

[75] Inventor: Robert W. Kalis, Mesa, Ariz.

[73] Assignee: Impra, Inc., Tempe, Ariz.

[21] Appl. No.: 134,072

[22] Filed: Oct. 8, 1993

[51] Int. Cl.[6] ............................................. A61F 2/06
[52] U.S. Cl. ............................................. 623/1; 623/12
[58] Field of Search ..................... 623/1, 12; 606/191, 606/194, 198

[56] References Cited

U.S. PATENT DOCUMENTS

| | | | |
|---|---|---|---|
| Re. 31,618 | 4/1984 | Mano et al. | 623/1 |
| 612,897 | 10/1898 | Ellis . | |
| 2,642,625 | 6/1953 | Peck | 18/47.5 |
| 3,008,187 | 11/1961 | Slade | 18/14 |
| 3,027,601 | 4/1962 | Barry | 18/57 |
| 3,060,517 | 10/1962 | Fields | 18/55 |
| 3,767,500 | 10/1973 | Tally et al. | 156/184 |
| 3,887,761 | 6/1975 | Gore | 174/110 R |
| 3,953,556 | 4/1976 | Gore | 264/288 |
| 3,962,153 | 6/1976 | Gore | 260/2.5 R |
| 4,049,589 | 9/1977 | Sakane | 260/2.5 M |
| 4,082,893 | 4/1978 | Okita | 428/376 |
| 4,118,532 | 10/1978 | Homsy | 428/294 |
| 4,159,370 | 6/1979 | Koizumi et al. | 526/73 |
| 4,177,334 | 12/1979 | Okita | 521/145 |
| 4,187,390 | 2/1980 | Gore | 174/102 R |
| 4,209,480 | 6/1980 | Homsy | 264/108 |
| 4,234,535 | 11/1980 | Okita | 264/519 |
| 4,248,924 | 2/1981 | Okita | 428/212 |
| 4,277,429 | 7/1981 | Okita | 264/127 |
| 4,279,245 | 7/1981 | Takagi et al. | 128/4 |
| 4,283,448 | 8/1981 | Bowman | 428/36 |
| 4,332,035 | 6/1982 | Mano | 623/1 |
| 4,437,206 | 3/1984 | Becker | 17/1 F |
| 4,478,665 | 10/1984 | Hubis | 156/229 |
| 4,478,898 | 10/1994 | Kato | 428/36 |
| 4,482,516 | 11/1984 | Bowman et al. | 264/127 |
| 4,550,447 | 11/1985 | Seiler, Jr. et al. | 623/1 |
| 4,588,461 | 5/1986 | Braun | 156/143 |
| 4,617,932 | 10/1986 | Kornberg | 128/344 R |
| 4,647,416 | 3/1987 | Seiler, Jr. et al. | 264/118 |
| 4,670,286 | 6/1987 | Nyilas et al. | 427/2 |
| 4,729,766 | 3/1988 | Bergentz et al. | 623/1 |
| 4,743,480 | 5/1988 | Campbell et al. | 428/36 |
| 4,753,833 | 6/1988 | Fishgal et al. | 428/36 |
| 4,796,629 | 1/1989 | Grayzel | 128/344 |
| 4,850,999 | 7/1989 | Planck | 623/1 |
| 4,955,899 | 9/1990 | Della Corna et al. | 623/1 |
| 4,957,669 | 9/1990 | Primm | 264/23 |
| 4,969,896 | 11/1990 | Shors | 623/1 |
| 5,061,276 | 10/1991 | Tu et al. | 623/1 |
| 5,123,917 | 6/1992 | Lee | 623/1 |
| 5,131,908 | 7/1992 | Dardik et al. | 600/36 |
| 5,178,630 | 1/1993 | Schmitt | 623/1 |
| 5,246,445 | 9/1993 | Yachia et al. | 606/108 |
| 5,282,847 | 2/1994 | Trescony et al. | 623/12 |
| 5,342,301 | 8/1994 | Saab | 604/96 |

FOREIGN PATENT DOCUMENTS

| | | |
|---|---|---|
| 0051955 | 5/1982 | European Pat. Off. .......... A61F 1/00 |
| 0051354 | 5/1992 | European Pat. Off. ....... A61M 25/00 |
| 13560/167 | 8/1967 | Japan . |

Primary Examiner—Michael J. Milano
Attorney, Agent, or Firm—David G. Rosenbaum

[57] ABSTRACT

A microporous reinforced expanded PTFE vascular graft in which the reinforcing structure is substantially identical in porosity to the body of the graft. The graft is characterized by a microporous expanded PTFE tubular graft wall and integral and monolithic expanded PTFE rib structures with a porosity or density substantially identical to that of the tubular graft wall.

18 Claims, 2 Drawing Sheets

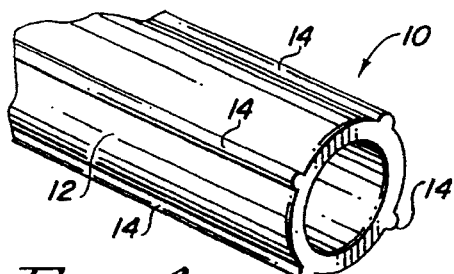
FIG. 1
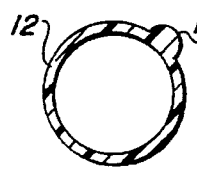 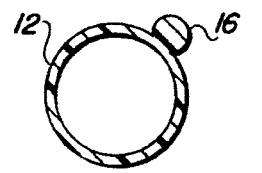  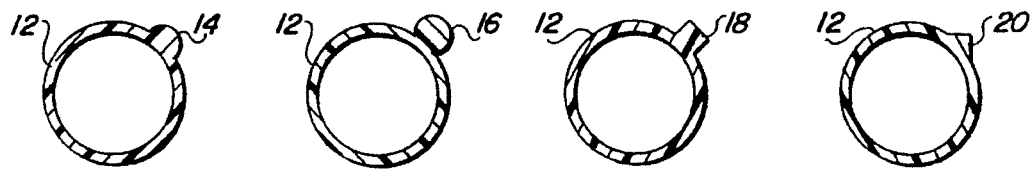
FIG. 2a  FIG. 2b  FIG. 2c  FIG. 2d
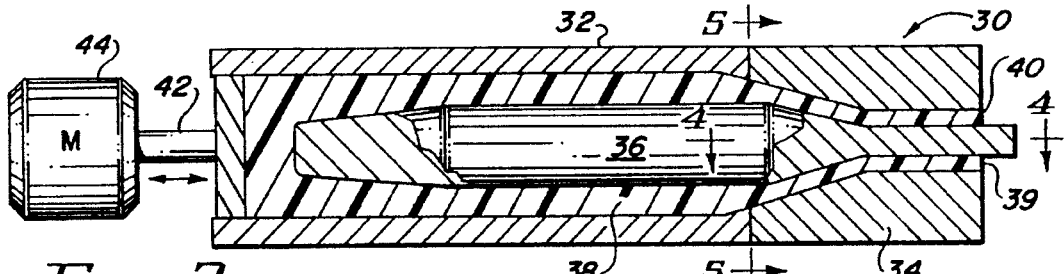
FIG. 3  FIG. 4  FIG. 5
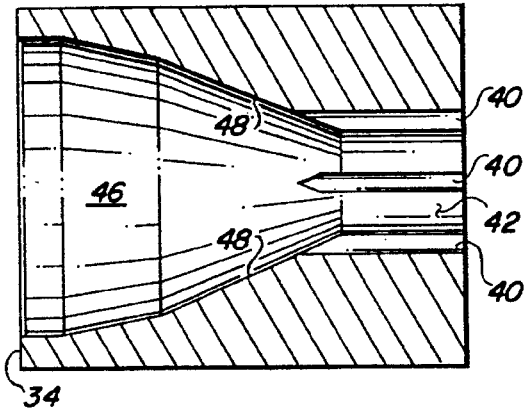 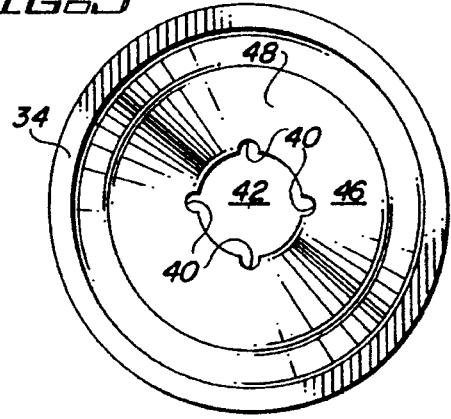
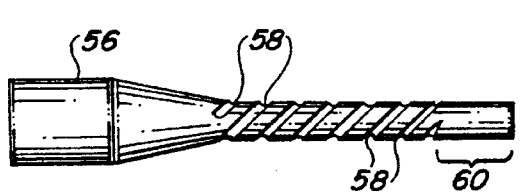 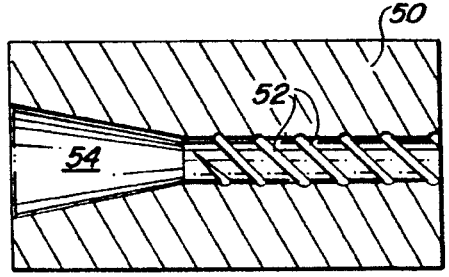
FIG. 6

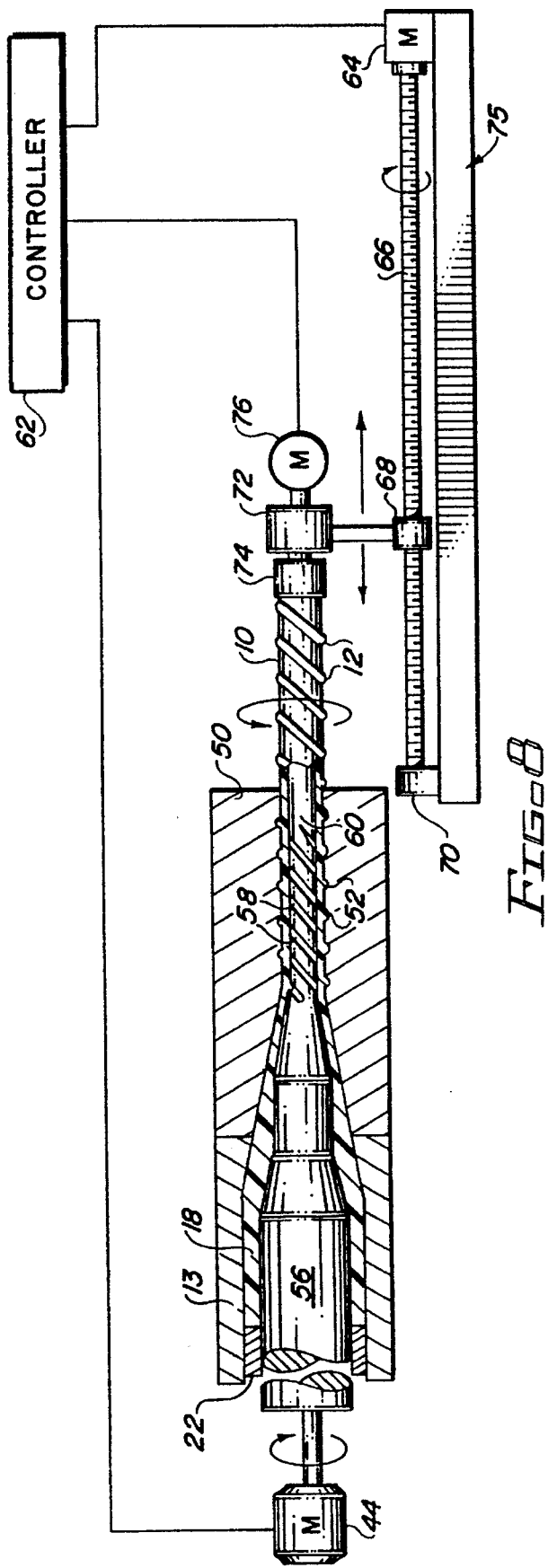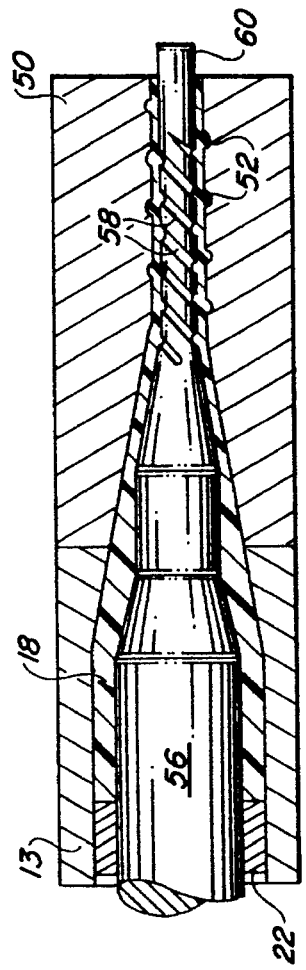

REINFORCED VASCULAR GRAFT AND METHOD OF MAKING SAME

BACKGROUND OF THE INVENTION

The present invention relates to generally to the field of porous vascular grafts. Specifically, it relates to polytetrafluoroethylene (PTFE) vascular grafts reinforced by integral helical ribs formed during extrusion of the vascular graft.

Synthetic vascular grafts are preferably characterized by being chemically inert, non-carcinogenic, non-antigenic to resist biodegradation or mechanical fatigue. Processes to make PTFE structures, including tubular structures, having a substantially uniform porous structure are exemplified by U.S. Pat. Nos. 3,953,566, 3,962,153 and 4,187,390 and Japanese Patent No. 13560/67, each of which are hereby incorporated by reference. Other processes for making PTFE vascular grafts having a porosity gradient through the tube wall are disclosed by U.S. Pat. Nos. 4,234,535 and 4,332,035. PTFE vascular grafts produced by any of the foregoing processes have received extremely favorable reception in the marketplace, but they lack resistance to kinking during, for example, joint articulation or external loading.

Radially reinforced vascular grafts are known in the art. For example, IMPRA, Inc., the assignee hereof, has for some time sold a porous expanded PTFE vascular graft having a helically wound bead of non-expanded PTFE on at least a portion of the longitudinal aspect of the graft under the trademark IMPRA FLEX and CENTERFLEX. U.S. Pat. No. 4,588,461 discloses a process for producing a vascular graft in which a tubular graft is mounted on a mandrel and axially rotated while a reinforcing thread is wound substantially tensionless on the tubular prosthesis. The reinforcing thread is adhered to the tubular graft by a solvent specific for the material of the reinforcing thread. A spacer band, insoluble in the thread solvent, is used as a carrier for the reinforcing thread. The wound graft is heated to remove the solvent and the spacer band is removed leaving the helically wound vascular graft. A similar type of wound bead is disclosed in U.S. Pat. No. 5,061,275. U.S. Pat. No. 4,969,896 discloses a reinforced vascular graft having discrete longitudinally oriented, radially spaced ribs on the outer peripheral surface of the tubular graft. The ribs are preferably made of solid silicone rubber. A sleeve or wrap is placed over the prosthesis such that it bridges between adjacent ribs defining spaces between the tubular graft and the wrap. The wrap is adhered to the graft by applying an adhesive bead. The tubular graft and the ribs are made separately as discrete components then the ribs are adhered to the outer peripheral surface of the tubular graft. These types of reinforced vascular grafts suffer from one or more difficulties, including, peeling or delamination of the reinforcing structure from the tube, compression of the unsintered graft which weakens the graft at the point of contact between the reinforcing structure and the tube, inability to suture the reinforcing structure, requiring removal of the reinforcing structure at the suture point, and potential contamination introduced by application of the reinforcing structure to the tube wall.

Moreover, none of the foregoing reinforced vascular grafts have microporous reinforcing structures. U.S. Pat. Nos. 4,550,447 and 4,647,416 disclose a ribbed porous vascular graft and a method for preparing a ribbed porous vascular graft, respectively. These patents teach that an expanded or unexpended PTFE tube may be scored in a regular and repeating pattern. The scored tube is then expanded below the sintering temperature of PTFE, thereby separating the scores into ribs, then sintering the scored, expanded tube while restraining the tube from axial shrinkage. The resulting graft creates ribs having a porosity less than that of the tube wall because the ribs are isolated from axial tension during sintering.

Heretofore, however, the prior art is devoid of a porous expanded reinforced PTFE tubular vascular graft in which the reinforcing structure exhibits substantially identical porosity as the tubular graft itself.

SUMMARY OF THE INVENTION

According to a broad aspect of the invention there is provided a microporous reinforced vascular graft in which the reinforcing structure is substantially identical in porosity to the body of the graft. More particularly, the present invention provides a microporous expanded PTFE vascular graft having reinforcing rib structures integral with the tubular graft with a porosity or density substantially identical to that of the tubular graft wall.

Another aspect of the invention is to provide alternative methods of making a microporous reinforced vascular graft. In accordance with a first method a PTFE billet is formed by mixing PTFE stock with an extrusion aid or lubricant, then ram extruding the billet through an extrusion die having a primary extrusion opening and at least one secondary extrusion opening contiguous with the primary extrusion opening. The resulting extrudate exhibits a tubular configuration having at least one axial rib along the length of the extrudate. The extrudate is then expanded according to known methodologies, except that one or both ends of the extrudate are radially rotated during expansion. The radial rotation during expansion winds the rib in a helical fashion along the length of the extrudate. Both ends of the wound extrudate are secured and axial tension applied. The extrudate is brought to sintering temperature while restraining the extrudate against shrinkage.

In accordance with a second method for making the microporous expanded PTFE reinforced vascular graft, a PTFE billet is formed by mixing PTFE stock with an extrusion aid or lubricant, then ram extruding the billet through an extrusion die having a helical groove in the inner peripheral surface of the die. The extrusion mandrel used to form the tubular structure has a helical thread-like projection which tapers to a smooth surface as the mandrel tip approaches the outlet opening of the die. During ram extrusion, the ram may be rotated in the direction of the helical groove in the die and the helical projection on the mandrel. The rotational movement of the ram imparts a rotational movement to the billet as it is being extruded. The extrudate issues from the outlet opening of the die and maintains rotational movement due to the projection in the mandrel and groove in the die. As the extrudate issues from the outlet opening, it is secured in a rotatable cuff mounted on a reciprocating carriage riding on a support rod. Axial movement of the carriage is coordinated with the extrusion speed to feed out at the same rate as the extrusion speed, thereby supporting the extrudate. The resulting extrudate exhibits a tubular configuration having at least one helical rib along the length of the extrudate. The extrudate is then expanded according to known methodologies while being secured against shrinkage in either the radial or axial direction except that one or both ends of the extrudate are radially rotated during expansion. If desired, the unsintered extrudate may undergo additional radial rotation during expansion to reduce increase the helical frequency of the ribs.

The reinforced vascular graft of the present invention is characterized by substantially uniform porosity throughout the tube wall and the reinforcing structure. This characteristic provides a greater porous surface area for tissue ingrowth on the abluminal surface of the graft. Further, handling of the graft during implantation procedures is enhanced over a non-beaded graft. Finally, in accordance with the second embodiment of the inventive method, the extrusion process orients the node and fibril structure of the PTFE at an angle relative to the longitudinal axis of the graft, which forms a helical node-fibril matrix. While the extrusion process differs from that disclosed in U.S. Pat. No. 4,743,480, angular displacement of the nodes has been demonstrated to increase matrix tensile strength, suture strength, water entry pressure, burst pressure and hoop strength, as those terms are defined in U.S. Pat. No. 4,743,480, which is expressly incorporated herein by reference.

These and other objectives, features and advantages of the present invention will be more apparent to those in the art from the following more detailed description of the preferred embodiments of the invention. The following description of the preferred embodiments references the accompanying drawings. Like features are identified by like reference numerals in the drawings.

BRIEF DESCRIPTION OF THE DRAWINGS

FIG. 1 is a perspective view of a reinforced vascular graft according to the present invention.

FIGS. 2a, 2b, 2c, and 2d are transverse cross-sectional views of alternative embodiments of the reinforced vascular graft of the present invention.

FIG. 3 is a diagrammatic cross-sectional view of a ram extruder and mandrel assembly for extrusion forming PTFE.

FIG. 4 is a cross-sectional view of an extrusion die used to form the reinforced vascular graft of the present invention taken along line 4—4 of FIG. 2.

FIG. 5 is an end elevational view of the extrusion die used to form the reinforced vascular graft of the present invention taken along line 5—5 of FIG. 3.

FIG. 6 is an exploded partial cross-sectional view of an extrusion mandrel and extrusion die used in an alternative embodiment of the method of the present invention.

FIG. 7 is a partial cross-sectional view of a ram extruder barrel, extrusion die and mandrel assembly used in the alternative embodiment of the method of the present invention.

FIG. 8 is a partial cross-sectional diagrammatic view of showing the ram extruder barrel, extrusion die and mandrel assembly of FIG. 6 operably associated with an extrudate take-up apparatus used to receive and support a tubular PTFE extrudate issuing from the ram extruder.

DETAILED DESCRIPTION OF THE PREFERRED EMBODIMENTS

FIG. 1 depicts a reinforced vascular graft 10 in accordance with the present invention. Reinforced vascular graft 10 consists of a microporous expanded PTFE tube 12 having at least one of a plurality of integral supporting structures, such as ribs 14, on the abluminal surface of the PTFE tube 12.

FIG. 2 illustrates transverse sections of alternative embodiments of the reinforced vascular graft 10. FIGS. 2a–2d illustrate alternative configurations for ribs 14. Ribs 14 may be configured to have semicircular transverse sections 14 (FIG. 2a), three-quarter circular transverse sections 16 (FIG. 2b), quadrilateral transverse sections 18 (FIG. 2c) or triangular transverse sections 20 (FIG. 2d). According to the best mode contemplated for the invention, it is thought that either the semicircular transverse section 14 or the triangular transverse section 20 are preferred configurations for rib 14 due to ease of manufacture of the extrusion die and regularity of surface area for tissue ingrowth.

FIG. 3 depicts a typical prior art ram extruder 10 used to form a PTFE vascular graft. The ram extruder 10 consists of an extrusion barrel 12, an extrusion die 14, a mandrel 16 around which a PTFE billet 18 flows under the influence of ram 20. Upon actuation of drive motor 24, ram 22 is driven hydraulically, pneumatically or electro-mechanically into barrel 12. The ram 22 exerts pressure on the PTFE billet 18 which causes the PTFE billet 18 be extruded around mandrel 16, through die 15 and issue as a tubular extrudate 20. Tubular extrudate 20 exhibits the shape of a typical elongated tubular vascular graft. The resulting PTFE tubular extrudate has an inside diameter ranging from 1.0 mm to 30 mm, and a length ranging up to 100 mm. The tubular extrudate is heated below the sintering temperature of PTFE, 327° C., to volatilize the lubricant used as an extrusion aid.

FIGS. 4 and 5 illustrate a first embodiment of an extrusion die 14 used to form the reinforced vascular graft of the present invention. Extrusion die 14 consists of a generally conical die having an extrusion chamber 46 defined by walls 48 which taper to an annular opening 42. Annular opening 42 has an inner peripheral wall demarcated by at least one groove 40 in the inner peripheral wall. Groove 40 is oriented axial relative to the longitudinal axis of the extrusion die, i.e., axial with the flow of PTFE through the extruder assembly 30. Groove 40 is formed with a selected transverse sectional shape as described above with reference to FIG. 2. The extrusion mandrel 36 projects concentrically into and through the annular opening 42 and defines the luminal surface of the tubular vascular graft extrudate issuing from annular opening 42. Those skilled in the art will appreciate that PTFE being extruded through the extrusion die 14 will assume the shape of annular space 39, including axial groove 40. Annular space 39, defined between the extrusion mandrel 36 and the annular opening 42, governs wall thickness of the resulting tubular vascular graft extrudate.

The tubular vascular graft extrudate issuing from the extrusion die 14 is transversely cut into individual sections of desired length. The lengths of tubular vascular graft extrudate are then mounted onto an expansion rack (not shown) as is well known in the art and described in U.S. Pat. No. 4,187,390, incorporated by reference.

The reinforced vascular graft 10 may be uniaxially expanded without radial movement displacement of the graft 10, or it may be uniaxially expanded while radially rotating one or both ends of the reinforced vascular graft 10. Straight longitudinal expansion yields a graft 10 having straight axial ribs 14. Radial rotation of one or both ends of the reinforced vascular graft 10 during uniaxial expansion imparts a helical wind to the at least one external rib 14 on the reinforced vascular graft 10. In both instances, the ribs 14 are an integral and monolithic part of the tube wall 12. Hence, the ribs 14 are expanded to the same degree as the tube wall 12 whether the graft 10 is uniaxially expanded with or without radial rotation.

The degree of radial rotation determines the helical frequency of the at least one external rib 14. Higher helical frequencies tend to lower the longitudinal compliance of the graft 10, while lower helical frequencies tend to increase longitudinal compliance. However, in both instances, the at least one external rib reinforces the tube wall 12 of the graft against crushing and kinking.

The ribs 14 have a resulting porosity substantially identical to that of the tube wall 12. According to the preferred embodiments of the invention, it is preferable to expand the graft 10 such that the average porosity of the graft 10, including both the wall 12 and the at least one rib 14, is between 30%–90%, preferably between 50%–85%, most preferably between 65%–85%. The porosity of the reinforced vascular graft 10 is achieved stretching the extrudate at an expansion ratio of about 50–5000%, preferably 150%–1000% at a temperature below 327° C, the sintering temperature of PTFE.

Radial rotation of the reinforced vascular graft 10 is accomplished by securing one or both ends of the graft 10 in a rotating clamp (not shown). The rotation of the rotating clamp may be achieved by a governing motor, through either a direct coupling or an indirect coupling such as gears or belts. Alternatively, if a rack and pinion-type expansion rack is employed, rotation of the rotating clamp may be accomplished through gearing coupled directly to the expansion rack.

After uniaxial expansion is complete, the expanded reinforced tubular graft 10 is clamped to secure against axial shrinkage and rotational unwinding, then heated to a temperature above the sintering temperature of 327° C.

FIGS. 6–8 illustrate a ram extruder assembly used in accordance with a second preferred embodiment of the inventive method. Under this second embodiment of the inventive method, a PTFE billet 18 is ram extruded through a barrel 12 and die 50 and around a mandrel 56 under the influence of a ram 22. However, unlike the first embodiment of the method, the die 50 has at least one helical groove 52 and the mandrel 56 has at least one rib-like helical projection 58 machined into their peripheral surfaces. The helical groove 52 in the extrusion die 50 is open at the issuing end of the extrusion die 50. The helical projection 58 in the mandrel 56, however, tapers to level at the peripheral surface of the mandrel forming a non-ribbed terminal end of mandrel 56 at the issuing end of the extrusion die 50. The non-ribbed terminal end 60 of mandrel 56 forms a macroscopically smooth luminal surface of the reinforced vascular graft 10.

Helical groove 52 and helical projection 58 preferably have a pitch angle between 15 and 165 degrees relative to the longitudinal axis of the extrusion die. To facilitate uniform angular displacement of the node-fibril arrangement throughout the wall thickness of the tube wall 12 and reinforcing ribs 14, the pitch angle and direction of helical groove 52 and helical projection 58 should be substantially identical. The groove 52 and rib-like projection 58 are preferably concentrically aligned to avoid shearing effects on the PTFE billet 18. To impart non-uniform angular displacement of the node-fibril arrangement throughout wall thickness of the tube wall 12 and reinforcing ribs 14, the pitch angle of helical groove 52 and helical projection 58 should be different, but the helical direction should be the same. It was posited in U.S. Pat. No. 4,743,480 that the relationship between node orientation at the lumenal and abluminal walls of tube 12 depends upon variables including relative pitch angle and direction of the helical groove 52 and helical projection 58.

To facilitate radial rotation of the PTFE billet 18 following helical groove 52 in the extrusion die 50 and the helical projection 58 on mandrel 56, it is preferable to rotate the ram 22 as it is forcing the billet 18 through the extrusion die 50. It should be understood that the rate of rotation of the ram 22 and the rate of extrusion may be controlled and coordinated with the helical frequency of helical groove 52 and and helical projection 58. By coordinating the rotational rate and the extrusion rate of ram 22 with the helical frequency of helical groove 52 and helical projection 58, the billet 18 undergoes bi-axial extrusion as it passes through the extrusion die 50.

As tubular extrudate 10, having ribs 12, issues from the extrusion die 50 it is undergoing radial rotation about the longitudinal axis of the tube. Once a sufficient length of tubular extrudate is exposed, the exposed end is coupled to an extrudate take-up apparatus 75. Extrudate take-up apparatus 74 supports the tubular extrudate 10 during extrusion, while permitting continuing rotational movement of the tubular extrudate 10 about its longitudinal axis. Extrudate take-up apparatus 75 includes a clamp 74 rotatably mounted in a clamp housing 72. The exposed end of tubular extrudate 10 is coupled to clamp 74 as it exits extrusion die 50. Clamp housing 72 is mounted on a reciprocating carriage 68, which undergoes longitudinal displacement under the influence of drive motor 64 and threaded support rod 66. The threaded support rod 66 is supported by a collet 70.

Clamp 74 may be freely rotatable in clamp housing 72 such that radial rotation imparted by the rotating ram 22 is unimpeded. Clamp housing 72 may also be operatively coupled to threaded support rod 66, e.g., by gearing, such that the longitudinal displacement of carriage 68 drives rotation of clamp 74 at the same rate of rotation as the ram 22. Alternatively, clamp housing 72 may be fitted with a dedicated drive motor 76 which coordinates the rotational rate of clamp 74 with the rotational rate of ram 22.

A controller 62 is preferably provided to dynamically coordinate extrusion rate, rotation rate of ram 22, the take-up rate of carriage 68 and, if employed, the rotation rate of drive motor 76.

EXAMPLE 1

A 1.5 inch diameter billet of PTFE was formed by compressing powdered PTFE admixed with an lubricating extrusion aid. The billet was extruded in a ram extruder having a barrel diameter of 1.5 inches, a mandrel tip diameter of 0.220 inches and an extrusion die opening diameter of 0.254 inches. The extrusion die was machined with four longitudinal circular grooves radially spaced at 90 degrees about the inner peripheral surface of the die opening. The billet was extruded at a rate of 0.2–0.3 mm/min. Twenty-one tubular extrudates were extruded, each having a length of 60 mm and four reinforcing ribs integral and monolithic with the abluminal surface of the tubular extrudates.

Group A, consisting of twelve tubular extrudates, were expanded at 260° C. using a straight longitudinal extrusion with no radial rotation. Group B, consisting of six tubular extrudates, were expanded at 200° C. using straight longitudinal extrusion with no radial rotation. Group C, consisting of three tubular extrudates, were expanded at 130° C. using straight longitudinal extrusion with radial rotation of one end of each tubular extrudate. Expansion for each of ribbed tubular extrudates of Groups A, B and C was 600%.

The tubular extrudates of Group C were expanded in step-wise 5 inch increments, with between one and three full revolutions of one end of the tubular extrudate made during each incremental 5 inch expansion. The reinforcing rib structures were expanded simultaneously with the tubular structure.

The resulting expanded PTFE tubular structures of Groups A, B and C were restrained against axial shrinkage, and those of Group C were restrained against helical unwinding, and then sintered at 375° C. The resulting grafts exhibited axial compliance and, when bent 180 degrees and crimped within about one inch of the resulting loop, were resistant to crushing and kinking like the reinforced grafts made by IMPRA, Inc. under the trademark IMPRA FLEX, consisting of non-expanded PTFE beading helically wound around an expanded PTFE tube or other prior art reinforced grafts.

Those skilled in the art will appreciate from the foregoing detailed description of the present invention with reference to its preferred embodiments, that the reinforced vascular graft of the present invention exhibits unique characteristics of strength, ease of handling and ease of manufacture. Those skilled in the art will appreciate that the described graft may be implanted in the same manner as is currently used to implant the reinforced vascular grafts of the prior art. While the invention has been described with reference to its preferred embodiments, the description is for illustrative purposes only and is not to be construed as limiting the spirit and scope of the invention. Various modifications and changes may be made by those skilled in the art without departing from the true spirit and scope of the invention as defined by the appended claims.

What is claimed is:

1. A flexible, monolithic, polymer tube, comprising:
   a microporous expanded polytetrafluoroethylene tubular member having a microstructure of nodes interconnected by fibrils and having an inner wall diameter and an outer wall diameter, and
   at least one microporous expanded polytetrafluoroethylene external rib member projecting outwardly from the outer wall diameter, the at least one expanded polytetrafluoroethylene external rib member being integral with the microporous expanded polytetrafluoroethylene tubular member, said microporous expanded polytetrafluoroethylene tubular member and said at least one expanded polytetrafluoroethylene external rib member having substantially equal porosities.

2. The flexible, monolithic, polymer tube according to claim 1, wherein the at least one external rib member has a semicircular cross-sectional shape.

3. The flexible, monolithic, polymer tube according to claim 1, wherein the at least one external rib member has a generally triangular cross-sectional shape.

4. The flexible, monolithic, polymer tube according to claim 1, wherein the at least one external rib member has a generally quadrilateral cross-sectional shape.

5. The flexible, monolithic, polymer tube according to claim 1, wherein the at least one external rib member has a generally circular cross-sectional shape.

6. The flexible, monolithic, polymer tube according to claim 1, wherein the microporous tubular member and the at least one external rib member each have an average porosity between 30–85%.

7. The flexible, monolithic, polymer tube according to claim 1, wherein the at least one external rib member is axially oriented along at least a longitudinal portion of the outer wall diameter of the microporous tubular member.

8. The flexible, monolithic, polymer tube according to claim 1, wherein the at least one external rib is helically disposed along at least a longitudinal portion of the tube wall.

9. A tubular vascular graft, comprising:
   a microporous tubular member having an inner wall surface and an outer wall surface and made of a biocompatible implantable microporous material, and
   at least one rib member being an integral part of, monolithic with and projecting outwardly along a longitudinal axis of the outer wall surface of the microporous tubular member, whereby microporous tubular member and the at least one rib member are made of the same biocompatible implantable microporous material and have substantially equal porosities.

10. The tubular vascular graft according to claim 9, wherein the microporous tubular member further comprises expanded PTFE.

11. The tubular vascular graft according to claim 10, wherein the at least one rib member further comprises expanded PTFE.

12. The tubular vascular graft according to claim 11, wherein the at least one rib member has a semicircular cross-sectional shape.

13. The tubular vascular graft according to claim 11, wherein the at least one rib member has a generally triangular cross-sectional shape.

14. The tubular vascular graft according to claim 11, wherein the at least one rib member has a generally quadrilateral cross-sectional shape.

15. The tubular vascular graft according to claim 11, wherein the at least one rib member has a generally circular cross-sectional shape.

16. The tubular vascular graft according to claim 11, wherein the microporous tubular member and the at least one rib member each have an average porosity between 30–85%.

17. The tubular vascular graft according to claim 9, wherein the at least one rib member is axially oriented along at least a longitudinal portion of the tube wall.

18. The tubular vascular graft according to claim 9, wherein the at least one external rib is helically disposed along at least a longitudinal portion of the tube wall.

* * * * *